(12) United States Patent
Fischer

(10) Patent No.: US 6,540,072 B1
(45) Date of Patent: *Apr. 1, 2003

(54) SYRINGE SET RACK SYSTEM AND RELATED METHODS

(75) Inventor: Dan E. Fischer, Sandy, UT (US)

(73) Assignee: Ultradent Products, Inc., South Jordan, UT (US)

(*) Notice: Subject to any disclaimer, the term of this patent is extended or adjusted under 35 U.S.C. 154(b) by 180 days.

This patent is subject to a terminal disclaimer.

(21) Appl. No.: 09/597,208

(22) Filed: Jun. 20, 2000

Related U.S. Application Data

(63) Continuation-in-part of application No. 09/455,552, filed on Dec. 6, 1999, now Pat. No. 6,283,946.

(51) Int. Cl.$^7$ .......................... B65D 83/10; A61M 5/315
(52) U.S. Cl. ........................................ 206/366; 604/218
(58) Field of Search ................................. 604/187, 191, 604/207, 208, 218, 220, 221, 225, 227–229, 235; D24/112, 113; 206/364–366, 370, 372, 558, 504, 505

(56) References Cited

U.S. PATENT DOCUMENTS

| | | | | |
|---|---|---|---|---|
| 570,936 A | * | 11/1896 | Lee | |
| 1,980,141 A | * | 11/1934 | MacGregor | |
| 2,856,067 A | * | 10/1958 | Sparks | |
| 3,074,540 A | * | 1/1963 | Beich et al. | |
| 3,133,635 A | * | 5/1964 | Gordon et al. | |
| 3,207,302 A | * | 9/1965 | Hobbs | |
| 3,255,873 A | * | 6/1966 | Speelman | |
| 3,305,084 A | * | 2/1967 | Higgins et al. | |
| 3,489,268 A | * | 1/1970 | Meierhoefer | |
| 3,727,749 A | * | 4/1973 | Martin | |
| 3,780,735 A | | 12/1973 | Crouter et al. | ............. 128/223 |
| 4,015,709 A | * | 4/1977 | Millet | |
| 4,142,633 A | * | 3/1979 | Raghavachari et al. | |
| 4,195,734 A | * | 4/1980 | Boner et al. | |
| 4,657,138 A | * | 4/1987 | Watson | |
| 4,753,345 A | * | 6/1988 | Goodsir et al. | |
| 4,846,797 A | * | 7/1989 | Howson et al. | |

(List continued on next page.)

OTHER PUBLICATIONS

US 1,277,455, 9/1918, MacGregor (withdrawn)

*Primary Examiner*—Sharon Kennedy
(74) *Attorney, Agent, or Firm*—Workman, Nydegger & Seeley

(57) ABSTRACT

A rack is provided for holding a set of syringes. The syringes may be conventional syringes or unique syringes that have a hollow elongated barrel engaged by a plunger with unique relative lengths. The rack is configured to rest on a flat surface and hold the syringes so that the syringes are horizontal relative to the flat surface for easy viewing. The rack has a series of cradles adapted to hold the barrels of syringes. Each cradle has a slot configuration with an open top, two opposing sides and a bottom surface so that all of the syringe barrel can be seen to enable a user to quickly identify the contents of the syringe based on indicia on the barrel. The cradles preferably have raised portions that act as locking extensions to provide a tight fit with the syringe barrel. Each cradle is separated from an adjacent cradle by a spacing element sized to prevent the grasping handle of a syringe from contacting the syringe barrel of an adjacent syringe for compact positioning without diminishing the accessability of the syringes. The thickness between each bottom surface of each cradle and the base surface of the rack is also preferably sized to avoid causing the accessability of the syringes to be encumbered by adjacent syringes. To optimally stack the rack on another rack, the racks preferably have stacking prongs extending from the spacing elements.

53 Claims, 10 Drawing Sheets

U.S. PATENT DOCUMENTS

| | | | |
|---|---|---|---|
| 4,863,451 A | * 9/1989 | Marder | |
| 4,925,449 A | 5/1990 | Saez | 604/227 |
| 4,974,728 A | * 12/1990 | Colton | |
| 4,986,820 A | 1/1991 | Fischer | 604/218 |
| 5,031,768 A | * 7/1991 | Fischer | |
| 5,048,684 A | * 9/1991 | Scott | |
| D322,317 S | 12/1991 | Fischer | D24/130 |
| 5,078,690 A | 1/1992 | Ryan | 604/187 |
| 5,133,454 A | * 7/1992 | Hammer | |
| 5,290,259 A | 3/1994 | Fischer | 604/218 |
| 5,328,462 A | 7/1994 | Fischer | 604/82 |
| 5,334,156 A | 8/1994 | Serrano Gonzalez | 604/110 |
| 5,522,503 A | * 6/1996 | Halbich | |
| 5,665,066 A | 9/1997 | Fischer | 604/82 |
| 5,697,903 A | 12/1997 | Fischer | 604/82 |
| 5,799,790 A | * 9/1998 | Ziegert et al. | |
| 6,135,984 A | 10/2000 | Dishler | 604/264 |
| 6,216,885 B1 | * 4/2001 | Guillaume | |
| 6,283,946 B1 | * 9/2001 | Fischer | |

\* cited by examiner

SYRINGE SET RACK SYSTEM AND RELATED METHODS

RELATED APPLICATIONS

This application is a continuation-in-part of U.S. patent application Ser. No. 09/455,552 filed Dec. 6, 1999, now U.S. Pat. No. 6,283,946 entitled Long Stem Syringe Apparatus for Dispensing Compositions and Related Methods. U.S. Pat. No. 6,283,946 was filed on behalf of Dan E. Fischer Dec. 6, 1999 and is assigned to Ultradent Products Inc. For purposes of disclosure of the present invention, U.S. Pat. No. 6,283,946 is incorporated herein by specific reference.

BACKGROUND OF THE INVENTION

1. The Field of the Invention

The present invention relates to a systems of syringes arranged for performing a procedure, preferably in sequential order. More particularly, the present invention is directed a system including a set of syringes and a rack configured to hold and display the set of syringes. Each syringe is preferably configured to deliver relatively small amounts such that the syringes are disposed of after a single use.

2. The Relevant Technology

Many dental procedures require the delivery of multiple compositions so several syringes are typically used. For example, when restoring a carious tooth with a composite filling the procedure may involve the use of a caries indicator, an etchant, a primer or bonding agent, a bonding resin, and a polymerizable composite. Such a procedure also typically involves the use of a polishing agent and a sealant. Due to the many compositions that are utilized in such procedures, there is a need for a system of organizing the various delivery devices. More particularly, a system is needed which reduces the time in between the steps of applying the various compositions.

The delivery devices used in such procedures are typically syringes. An example of a widely used conventional syringe is shown in FIGS. 2A–2D at 100. Although such a syringe is very useful as a delivery device in many procedures, particularly dental procedures, some circumstances require the use of uniquely configured syringes. For example, many dental procedures are optimally performed with enhanced delivery control. Additionally, it is often preferable to deliver very small amounts of a liquid from a syringe which can then be disposed of after a single use. Accordingly, syringes are also needed which enable small amounts to be delivered from single use disposable syringes that enable a user to have a high degree of control during delivery.

In conclusion, a system is needed for supporting a set of syringes in an organized arrangement. The system needs to allow the syringes to be easily fully viewed when held by a display and holding device and to be easily removed and returned to the device. Such a system is needed for conventional syringes and also for syringes designed for single use so that the entire system is disposable.

OBJECTS AND BRIEF SUMMARY OF THE INVENTION

Accordingly, it is a primary object of the present invention to provide improved systems and methods for organizing various delivery devices used in a particular procedure, especially systems and methods that reduces the time in between the steps of applying the various compositions.

Another object of the present invention is to enable a user to easily view the syringes held in a rack and to enable a user to easily remove and return the syringes to a rack.

An additional object of the present invention is to provide systems and methods for supporting a set of syringes sized for single use in an organized arrangement so that the entire system is disposable.

Yet another object of the present invention is to provide systems and methods for enabling a user to deliver small amounts from single use disposable syringes that also enable a user to have a high degree of control during delivery.

Finally, an object of the present invention is to provide methods and apparatus for enabling a practitioner to easily apply adequate amounts of pressure to dispense a composition as desired without regrasping the syringe during the depression of the plunger into the barrel such that the syringe is not moved relative to a delivery site during the delivery of the composition to the delivery site due to movement of the user's hand.

Additional objects and advantages of the invention are set forth hereinbelow in the detailed description, or will be appreciated by the practice of the invention.

To achieve the foregoing objects, and in accordance with the invention as embodied and broadly described herein, the present invention provides a novel rack adapted for holding a set of syringes. The syringes may be conventional syringes or unique syringes that have a hollow elongated barrel engaged by a plunger with unique relative lengths.

The rack is configured to rest on a flat surface and hold the syringes so that the syringes are horizontal relative to the flat surface. So if a user has the rack resting on a table the entire syringe can be easily viewed. More importantly, the syringe barrel of each syringe can be seen and the printed indicia can be easily read.

The rack and the set of syringes held in the rack may be used in various procedures, however, dental procedures are particularly benefitted by the use of the rack and the set of syringes. Dental procedures such as procedures related to the restoration of a tooth typically involve the use of several different compositions that are sequentially delivered from different syringes. The systems and methods disclosed herein are very useful for such procedures as the syringes are held in manner that enables the practitioner to easily remove each syringe from the rack and return each syringe to the rack in a sequential manner such that the time in between the steps of applying the various compositions is minimized.

The rack has a series of cradles adapted to holding the barrels of syringes. The cradles conform to the configuration of the syringe barrels which are typically round. Each cradle has a slot configuration with an open top, two opposing sides and a bottom surface. Since the cradle holds the syringe in an open configuration all of the syringe barrel can be seen. So a user can quickly identify the contents of the syringe based on indicia such as the printed material on the barrel, the color of the barrel, the color of the plunger, etc.

Each cradle preferably has a locking extension that extends from both sides of the cradle. The locking extensions are raised portions that extend slightly beyond the surface of the sides to provide a tight fit with the syringe barrel. This tight fit between enables the syringe barrels to be held in place as the rack is moved with the set of syringes during transportation and use.

Each cradle is separated from an adjacent cradle by a spacing element. The spacing elements have a width or thickness that is at least about the same as or slightly greater than the length of elements extending from the syringes. More particularly, the grasping handle of each syringe is prevented from contacting the syringe barrel of an adjacent syringe due to the length of the spacing elements.

Accordingly, syringes can be positioned close together without diminishing the accessibility of the syringes.

The thickness between each bottom surface of each cradle and the base surface of the rack is preferably about the same as or greater than the length that each grasping handle extends from each syringe barrel. This configuration prevents the syringes from being pivoted out of the cradles when the rack is placed on a flat surface. Also when several racks are stacked on each other, this configuration prevents the grasping handles of the syringes in one set from becoming encumbered by the grasping handles of the syringes in the adjacent set.

To optimally stack the rack on another rack, the racks preferably have stacking prongs extending from the spacing elements. The optional prongs are preferably at the opposing ends of the rack.

The syringes used with the rack may be conventional syringes or syringes that are uniquely configured for delivery of small amounts of a composition in a unidose or single application. The chamber of the syringe barrel is preferably sized to hold just enough composition for use in a single dental restorative procedure. The small size of the syringe barrel enables less plastic material to be used so that the syringes can be disposed of after a single use.

In contrast to prior art syringes which have chambers and plungers with approximately the same lengths, the plunger has a length that is significantly longer than that of the chamber of the barrel. The plunger preferably has a length that is at least twice that of the chamber of the barrel. Accordingly, when the plunger is fully advanced within the chamber a portion of the plunger extends out of the chamber with a length that is preferably at least equal to that of the chamber. The length of the plunger relative to that of chamber enables the syringe to be grasped in a single position and then to be used to continuously deliver the composition by advancing the plunger within the chamber until the composition is expressed from the chamber. This is a significant advantage as it eliminates the possibility of accidentally moving the syringe due to altering one's grasp of the syringe. It is typically necessary to regrasp prior art syringes as the plunger is depressed within the barrel. Not only is it unnecessary to regrasp the syringe during the depression of the plunger into the chamber, the configuration of the syringe also enables a user to exert less effort in delivering the composition. Further, the configuration enables a user to exert essentially the same amount effort throughout the depression of the plunger within the chamber of the barrel, thereby avoiding the possibility of suddenly varying the delivery rate.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained will be understood, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings as listed hereinbelow.

DETAILED DESCRIPTION OF THE PREFERRED EMBODIMENTS

The present invention relates to a systems of syringes arranged for performing a procedure, preferably in sequential order. More particularly, the present invention is directed to a system including a set of syringes and a rack configured to hold and display the set of syringes. The syringes in the set may be any conventional syringes. However, the syringes in the set are preferably configured to deliver relatively small amounts such that the syringes are disposed of after a single use.

Figure 1A:
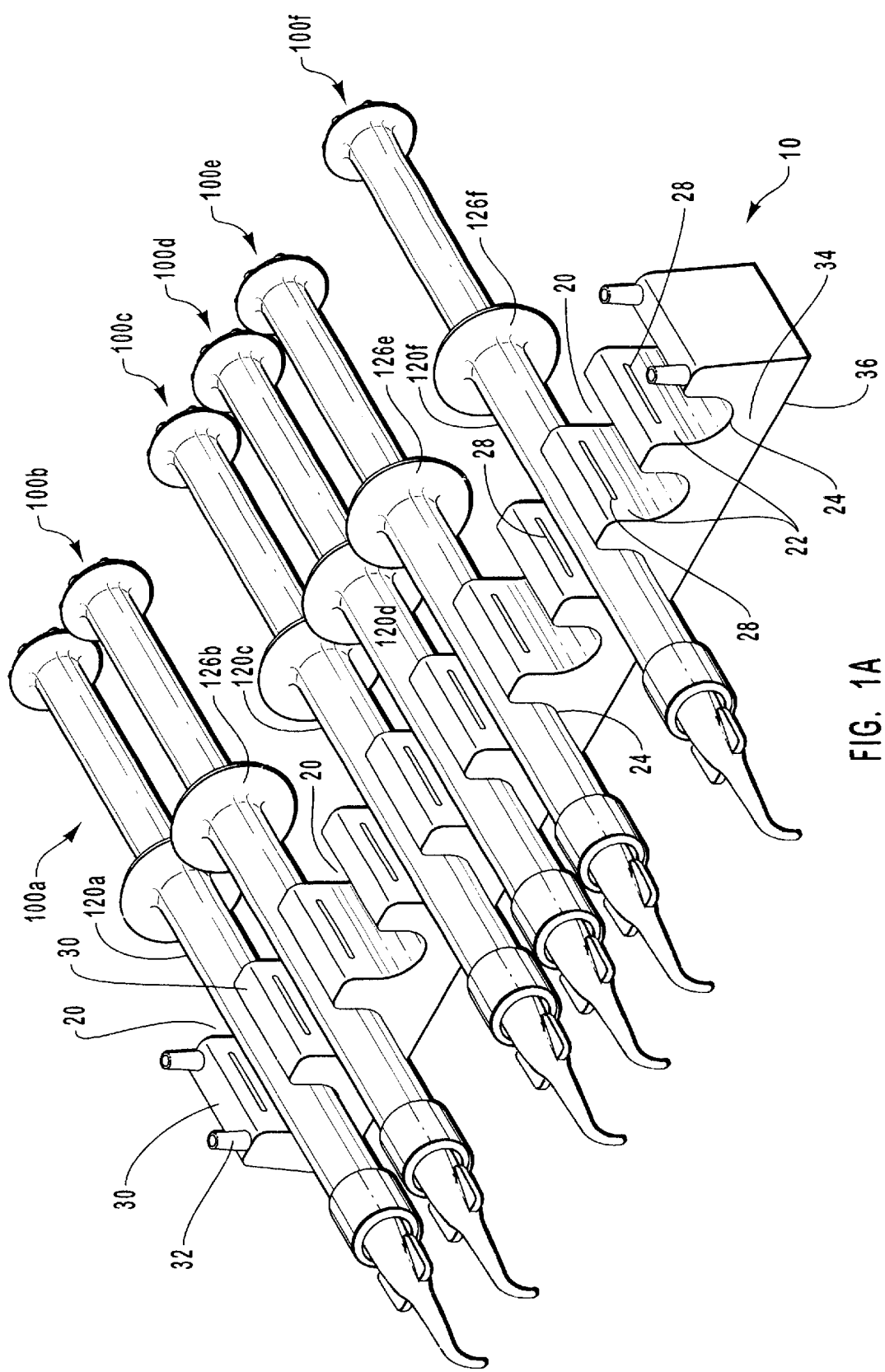
FIG. 1A is a perspective view of a rack 10 holding a set of syringes 100a–f.

FIG. 1A depicts a set of conventional syringes 100a–f being held by syringe rack 10. Rack 10 has a series of cradles 20 adapted to holding the barrels of syringes. Cradles 20 are preferably rounded as shown in order to conform to the typically round configuration of syringe barrels. More particularly, each cradle preferably has two opposing sides 22 with a curved bottom surface 24. An advantage of this open configuration is that each syringe is held securely by its barrel in one of the cradles in manner that enables all of the barrel to be simultaneously viewed. So a user can quickly identify the contents of the syringe based on indicia such as the printed material on the barrel, the color of the barrel, the color of the plunger, etc.

Note that the length of each cradle is less than about half of the length of the syringe is barrels 120. This length is sufficient to maintain a syringe in a horizontal position relative to the cradle and also ensures the easy removal of a syringe from the cradle.

Each cradle 20 preferably has a locking extension 28 that extends from both sides 22 of the cradle. The locking extensions 28 are raised portions that extend slightly beyond the surface of sides 22 such that there is a tighter fit with the syringe barrel as compared with the fit between the syringe barrel and the lower portion of sides 22 when the syringe barrel 120 is resting on bottom surface 24. The fit between locking extension 28 and syringe barrel 120 enables the syringe barrels to be held in place as rack 10 is moved with the set of syringes 100a–f. More particularly, the fit is preferably sufficiently tight that rack 10 may be moved in any direction without displacing syringes 100a–f including moving the rack such that it is upside down as shown in the bottom view depicted in FIG. 1B.

Each cradle is separated from an adjacent cradle by a spacing element 30. As shown in FIG. 1C, the width or thickness of spacing elements 30 is about the same as or slightly greater than the length that each grasping handle 126 extends from each syringe barrel 120. More particularly, the grasping handle 126 of one syringe 100 almost contacts the barrel 120 of the adjacent syringe. As a result, the syringes can be positioned close together as shown in FIG. 1A. For example, grasping handle 126d of syringe 100d is shown in FIG. 1A spaced about 1 mm or less from barrel 120c of syringe 100c. The spacing element may, however, have any suitable width. As discussed below, an example is provided in FIGS. 6A–6D of an embodiment of a rack with wider spacing elements.

Figure 1B:
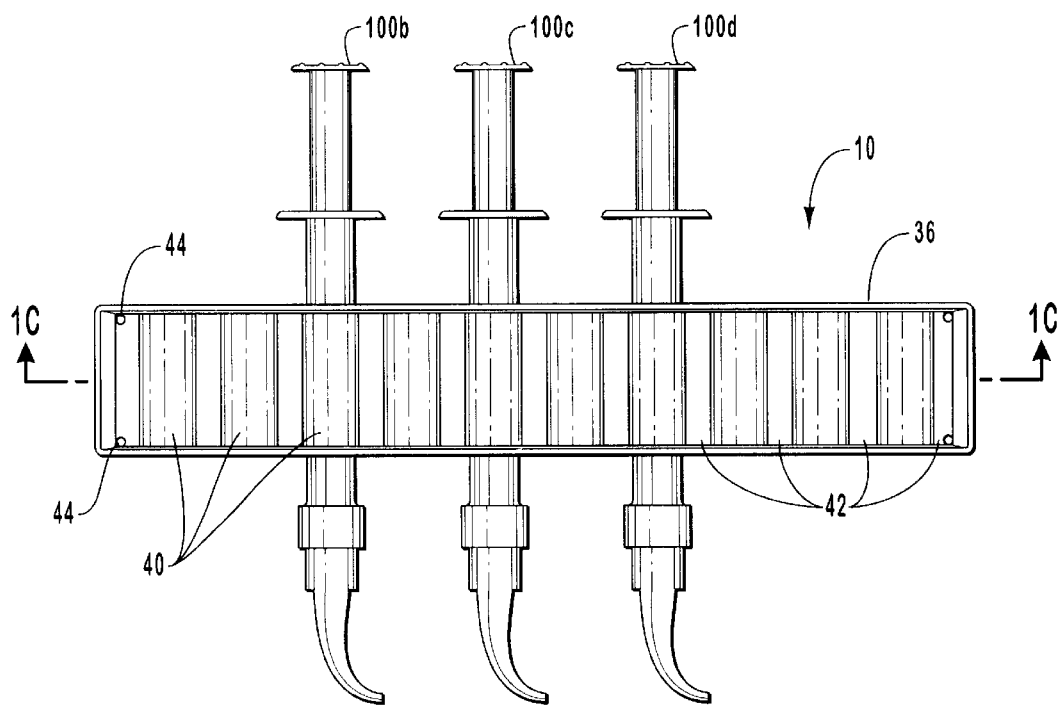
FIG. 1B is a bottom view of rack 10.
Figure 1C:
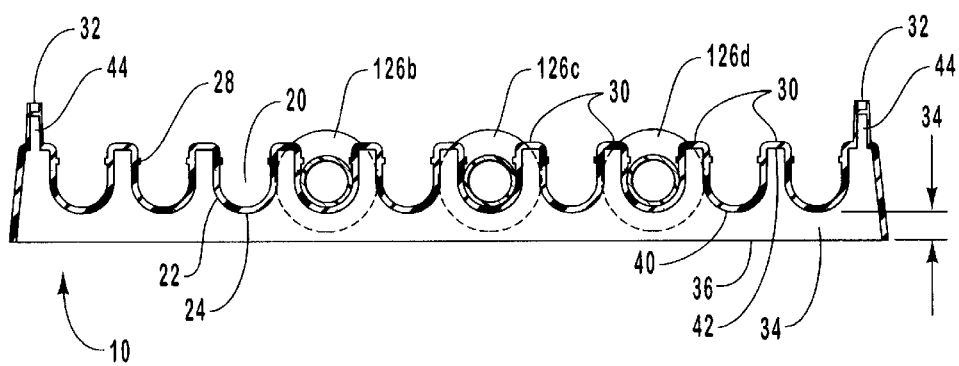
FIG. 1C is a longitudinal cross-sectional view of rack 10.
Figure 1D:
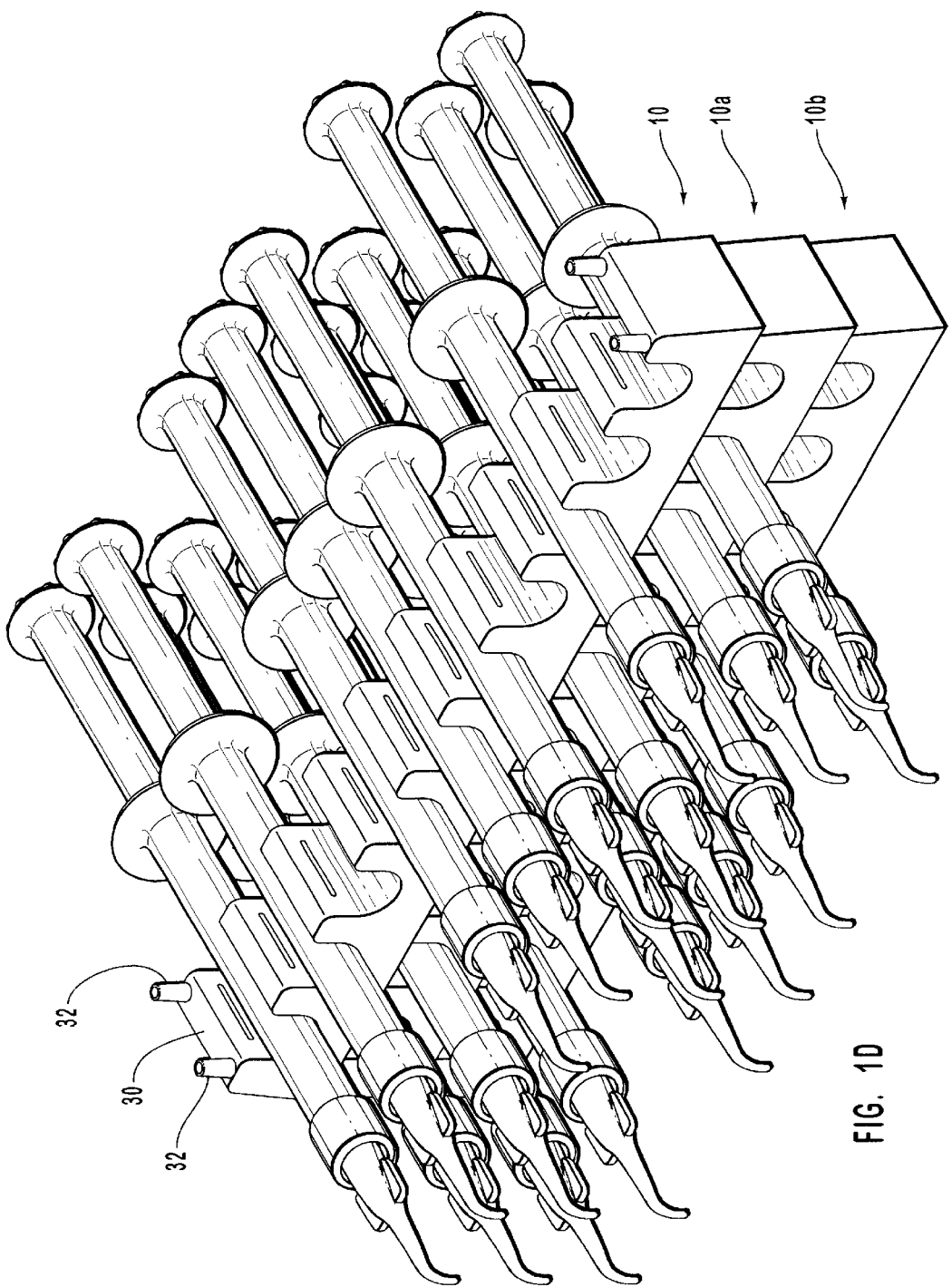
FIG. 1D is a perspective view of a rack 10' stacked on rack 10a which is on rack 10b.

FIGS. 1B and 1C depict rack 10 with only three syringes instead of six syringes as in FIGS. 1A and 1D. The number of syringes in the set varies depending on the particular procedure that the set is used to complete, as described below in greater detail. As indicated above, FIG. 1B depicts the bottom view of rack 10. From this view it is evident that rack 10 is hollow. The hollow configuration reduces the manufacturing costs. Rack 10 can also alternatively be formed to be solid. When rack 10 is hollow, as shown, the bottom side of each cradle 20 appears as a rounded swell 40 and the bottom side of each spacing element 30 appears as a flat surface 42.

As shown in FIG.s 1A and 1C, rack 10 preferably has stacking prongs 32 extending from the spacing elements 30 at the opposing ends of rack 10. The optional prongs 32 enable a series of racks 10, 10a, 10b to be stacked on top of each other as shown in FIG. 1D. The optional stacking prongs are preferably hollow such that each stacking prong has a recess 44 as shown in FIGS. 1B and 1C.

Note that the thickness between each bottom surface 24 of each cradle 20 and base surface 36, as best viewed in FIG. 1C, is about the same as or greater than the length that each grasping handle 126 extends from each syringe barrel 120. This configuration prevents the syringes 100 from being pivoted out of the cradles when rack 10 is placed on a flat surface. Also when several racks are stacked on each other as shown in FIG. 1D, this configuration prevents the grasping handles 126 of the syringes in one set from becoming encumbered by the grasping handles 126 of the syringes in the adjacent set. Accordingly, the thickness of platform portion 34 enables the racks 10 to be stacked without altering the position of the syringes 100 as shown in FIG. 1D.

As mentioned above, FIG. 1A and FIG. 1D depicts rack 10 holding six syringes 100a–f while FIG. 1B and FIG. 1C depict three syringes 100a–c. Rack 10 may be designed with less cradles 20 when used with a relatively small number of syringes such as three syringes or three syringes may be merely spaced apart from each other as shown in FIG. 1B and FIG. 1C. Rack 10 may hold syringes for use in many different procedures. However, rack 10 preferably holds syringes arranged for sequential use in a procedure requiring use of different compositions held in different syringes. Such a system is particularly useful for many dental procedures.

An example of a dental procedure that may be beneficially performed in accordance with the present invention through using syringes sequentially arranged in rack 10 is a dental restoration procedure, especially a dental restoration procedure that is achieved with dental composite material. As indicated above, restoration of a carious tooth with a composite filling typically involves the use of a caries indicator, an etchant, a primer or bonding agent, a polymerizable composite, a polishing agent and a sealant. If syringes 100a–f shown in FIG. 1A and FIG. 1B are filled with such dental compositions then syringe 100a holds a carious indicator such as SEEK® caries indicator sold by ULTRADENT PRODUCTS, INC., syringe 100b holds an etchant such as ULTRA-ETCH® etchant sold by ULTRADENT PRODUCTS, INC., syringe 100c holds a bonding agent such as PQ1® bonding agent sold by ULTRADENT PRODUCTS, INC., syringe 100d holds a flowable composite such as PERMAFLOW® flowable composite sold by ULTRADENT PRODUCTS, INC., syringe 100e holds a polishing agent such as ULTRADENT® DIAMOND POLISH sold by ULTRADENT PRODUCTS, INC., and syringe 100f holds a sealant such as PERMASEAL® sealant sold by ULTRADENT PRODUCTS, INC.

Of course some circumstances do not require the use of all of these components. For example, a dental restoration procedure may be completed by utilizing only a bonding agent and a flowable composite so that the rack need only hold two syringes. However, such a dental restoration procedure more typically involves the use of an etchant in preparation for bonding. When an etchant, a bonding agent and a flowable composite are utilized then only three syringes are utilized. This number of syringes can be expanded to four syringes when the bonding agent is replaced with a different bonding system that requires delivery of two separate chemicals such a bonding primer and a bonding resin as opposed to a single bonding agent. A preferred two component bonding system is the PERMAQUI-CK® bonding primer and PERMAQUICK® bonding resin sold by ULTRADENT PRODUCTS, INC. When using such a bonding system, along with a caries indicator, a polishing agent and a sealant then seven syringes are required. In any event, rack 10 may be utilized with varying number of syringes as required by the particular procedure and may be actually configured on a tailored basis to have a number of cradles corresponding to the number of syringes involved in the procedure or there may be some cradles that are unused as shown in the drawings.

Dental procedures such as restoration procedures involving use of composite materials to fill the preparation are typically performed with syringes such as syringe 100. However, such procedures may also be performed with a syringe such as syringe 200 shown in FIGS. 3A–3D and in FIGS. 6A–6D with rack 10'. Syringe 200 has several advantages over syringe 100 that enable syringe 200 to be particularly useful with a rack such as rack 10 or rack 10'. The primary advantage of syringe 200 is that it is specifically designed for a single use. Accordingly, each syringe in the system that is held by rack 10 may be used and then the entire system including rack 10 and the syringes may be disposed of after a single use. Another advantage of syringe 200 is enhanced delivery control.

To appreciate the differences between syringe 100 and syringe 200, it is necessary to first understand the configuration of a conventional syringe such as syringe 100. The elements of such a syringe are briefly described hereinbelow in reference to FIGS. 2A–2D.

The main components of syringe 100 are of course the barrel 120 and the plunger 150 that is slidably engaged in barrel 120. Barrel 120 has a top grasping end 121 opposite a bottom end 129 with a substantially cylindrical sidewall 122 extending therebetween. Sidewall 122 has an exterior surface 123 and an interior surface 124. Interior surface 124 defines a substantially cylindrical chamber 125 for holding a composition. Chambers such as chamber 125 of barrel 120 are typically configured to hold about 1.2 cc of liquid.

Barrel 120 has a grasping handle 126 which is an annular flange extending radially outward from sidewall 122 at top grasping end 121 of barrel 120. Grasping handle 126 is centrally located around opening 127 which has the same diameter as the interior surface 124 of chamber 125.

A radial extension 128 extends integrally from sidewall 122 at bottom end 129 inward to define an exit port 132. Radial extension 128 acts as a stop for plunger 150 as plunger 150 is depressed.

Exit port 132 is the opening into channel 133 which enables channel 133 to communicate with chamber 125. Note that channel 133 is the interior surface of tapered exit tube 130. Channel 133 extends through tapered exit tube 130 and terminates at outlet 134.

Surrounding exit tube 130 is an attachment sleeve 136. Attachment sleeve 136 has an interior surface 137 with engagement threads 138 positioned thereon. A nozzle or tip 140, shown in FIGS. 2C and 2D, may be selectively attached to barrel 120 by coupling with threads 138. A variety of tips are available which may be attached such that channel 133 of exit tube 130 is in fluid communication with the tip for guided delivery of the composition to a desired location.

Tip 140 is configured to selectively attach in fluid communication with exit tube 130. To accomplish this end, tip 140 has a threaded end 142 for engagement with threads 138 of attachment sleeve 136. Opposite threaded end 142 is a flexible and angled spout 144 for guiding delivery of the composition to a desired location. Of course different sizes and shapes of spouts can be used depending on the type and intended use of the composition. Furthermore, in alternative embodiments, tip 140 may be permanently attached to bottom end 129 or mechanisms other than threads may be used to attach different sizes and/or shapes of tips.

Plunger 150 has a distal lead end 151 opposite from a proximal pushing end 153 with a stem 152 extending therebetween. Radially extending outward at pushing end 153 is an annular pushing handle 158 used in advancing plunger 150. Plunger 150 is sized to be slidably received within chamber 125 through opening 127 at top grasping end 121. Plunger 150 has a length that permits it to be advanced to bottom end 129 such that a small portion of plunger 150 remains extending beyond opening 127.

Figure 2A:
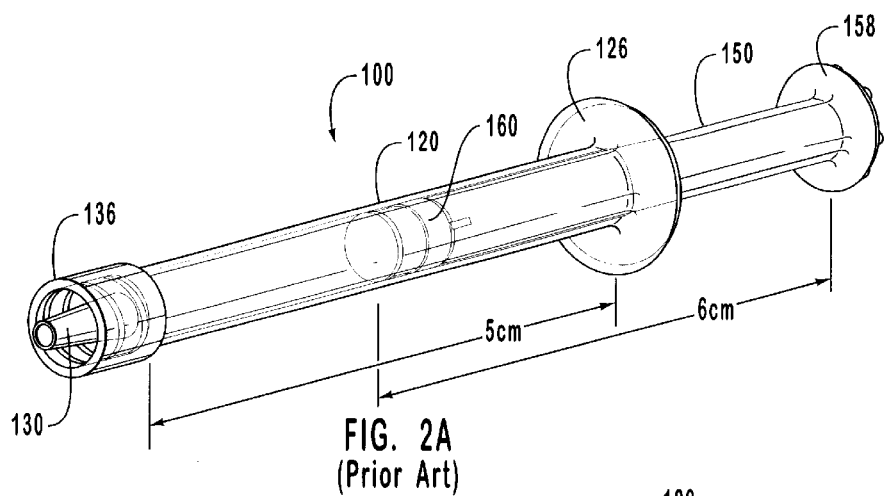
FIG. 2A is a perspective view of a conventional syringe 100.
Figure 2B:
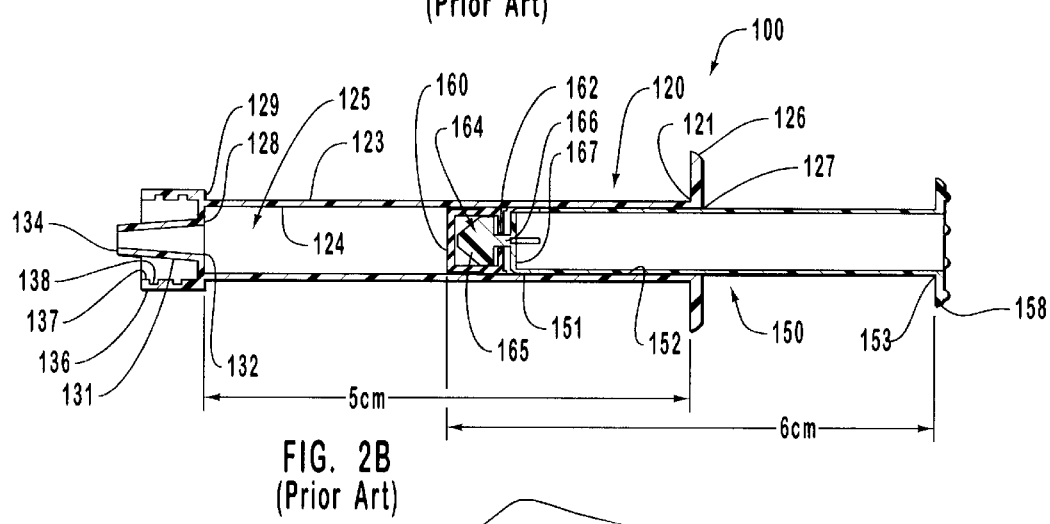
FIG. 2B is a cross-sectional view of the syringe 100 shown in FIG. 2A.

Positioned at lead end 151 of plunger 150 is a cylindrically shaped sealing gasket 160. More particularly, gasket 160 is coupled to stem 152 via a gasket holder as shown in FIG. 2B at 164. Gasket 160 is made of a soft, compressible, sealing material, such as rubber, which allows the exterior surface of gasket 160 to seal against interior surface 124 of chamber 125 as plunger 150 is advanced within chamber 125 or selectively slid down to bottom end 129. Gasket bolder 164 has a post 166 with a head element 165 integrally extending at one end and a base 167 integrally extending from the other end. Head element 165 and post 166 are inserted into an opening 162 of gasket 160 which expands such that head element 165 can be inserted therein and then elastically return to its original size such that head element 165 is removably held in gasket 160. Base 167 is connected to stem 152 to hold gasket holder 164 in position.

Figure 2C:
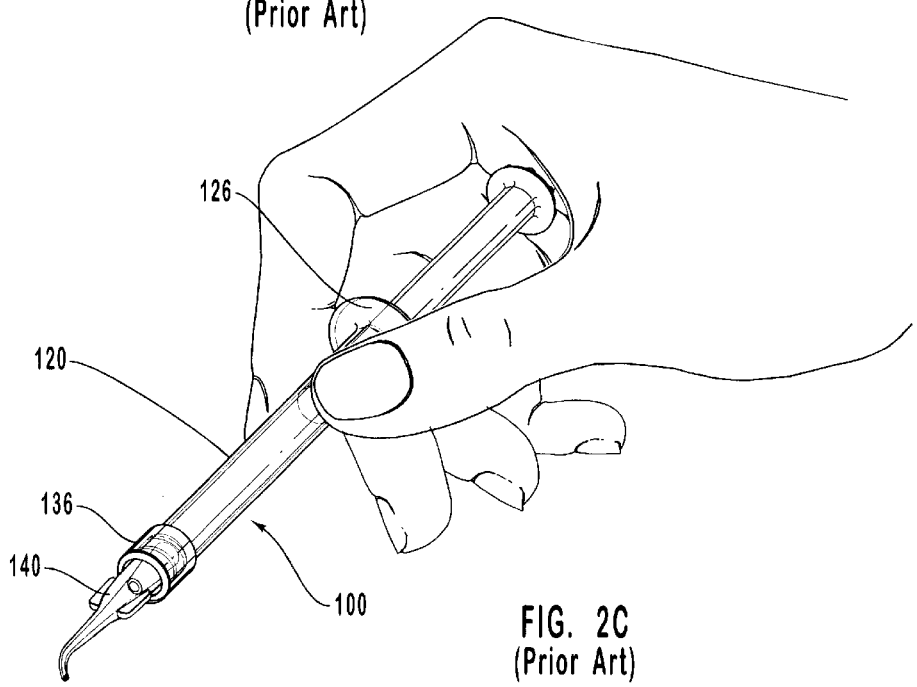
FIG. 2C is a perspective view of the syringe 100 shown in FIG. 2A loaded with a composition and with the plunger positioned to initially express the composition from the syringe.
Figure 2D:
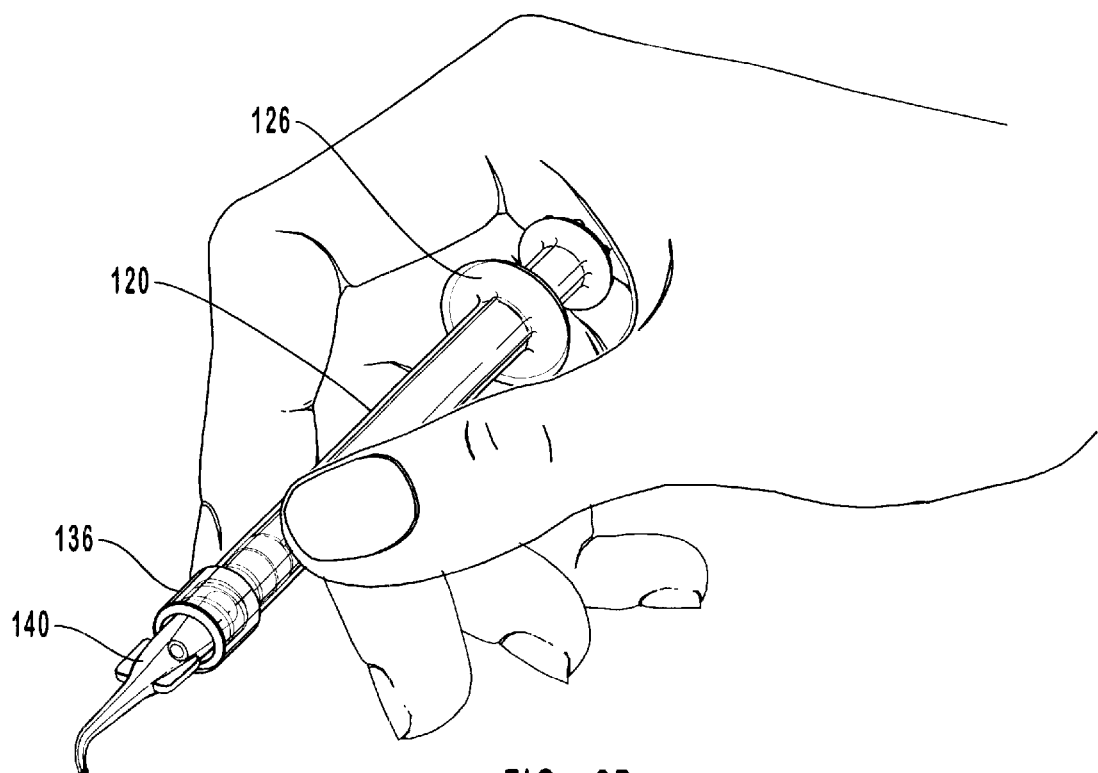
FIG. 2D is a perspective view of the syringe 100 shown in FIG. 2A after the plunger has been fully depressed to express all of the composition from the syringe.

As discussed above, a small portion of plunger 150 remains extending beyond opening 127, as shown in FIG. 2D, when plunger 150 has been fully depressed such that gasket 160 contacts radial extension 128. The length of the portion of plunger 150 extending beyond opening 127 of syringe 100 when plunger 150 is fully depressed is about 1 cm. This configuration is typical for a conventional 1.2 cc syringe. Note that the length of the barrel is about 5 cm while the length of the plunger which includes gasket 160 is about 6 cm such that the ratio of the length of the plunger to the length of the chamber is 1.2:1.

While syringes such as syringe 10 are ideal for many uses, these syringes also have certain limitations. For example, in some instances it can be difficult to apply an adequate amount or the appropriate amount of force required to push the composition from chamber 125 into channel 133 and ultimately out of tip 140 attached to barrel 120. FIG. 2C depicts a loaded syringe with only gasket 160 and a portion of stem 152 in chamber 125 of barrel 120. As shown in FIG. 2C, a user typically grasps syringe 100 such that barrel 120 is held by the user's middle and index fingers as well as the user's thumb. As the plunger is depressed further and further into chamber 125 until gasket 160 contacts radial extension 128 to stop the depression of plunger 150 as shown in FIG. 2D, the user may have to exert increasing effort to dispense the composition. Accordingly, it becomes difficult to dispense the composition at a uniform rate and in a controlled manner. When a composition is relatively viscous, the difficulty experienced in applying either an adequate amount or the appropriate amount of force may further increase.

When an inappropriate amount of force is applied to pushing handle 158, gasket 160 may press against sidewall 122 of chamber 125 in a manner such that plunger 150 is not smoothly pushed into chamber 125 in a controlled manner. Plunger 150 may stop and then suddenly move downward in what is known as a stuttering effect. This can potentially result in delivery of excessive amounts of a composition which the practitioner is attempting to deliver in a discrete amount.

As indicated above, FIGS. 3A–3D illustrate a syringe 200 which is useful for dispensing compositions in accordance with the present invention. Syringe 200 is shown having a barrel 220 with a plunger 250 slidably engaged therein. Note that in contrast to syringe 100 shown in FIGS. 2A–2D, barrel 220 is much shorter than barrel 120. More particularly, barrel 220 is shown having a length which is almost half that of barrel 120. Accordingly, plunger 250 is much longer than barrel 220. Although the advantages of this configuration are fully related below it should be understood that the primary advantage resulting from this configuration is that a user can grasp the syringe and express all of the composition contained in the syringe without having to change the grasping position.

As also discussed in greater detail hereinbelow, barrel 220 is adapted for unidosing so that its contents are dispensed in a single use. The syringe may then be discarded along with rack 10 and the other syringes once each syringe has been used. Other features will be appreciated after understanding the details of the elements of syringe 200 as set forth hereinbelow. The components of syringe 200 are essentially identical to those of syringe 100 with the exception of the barrel lengths. Barrel 220 is much shorter than barrel 120. Although the components are essentially identical, the components of syringe 200 are also described in detail to provide a complete description of syringe 200. Note that the components of syringe 200 that are similar or identical to those of syringe 100 are numbered similarly with a difference of 100.

Barrel 220 has a top grasping end 221 opposite a bottom end 229 with a substantially cylindrical sidewall 222 extending therebetween. Sidewall 222 has an exterior surface 223 and an interior surface 224. Interior surface 224 defines a substantially cylindrical chamber 225 for holding a composition. Cylindrical chamber 225 is discussed in greater detail hereinbelow in reference to plunger 250.

Figure 4:
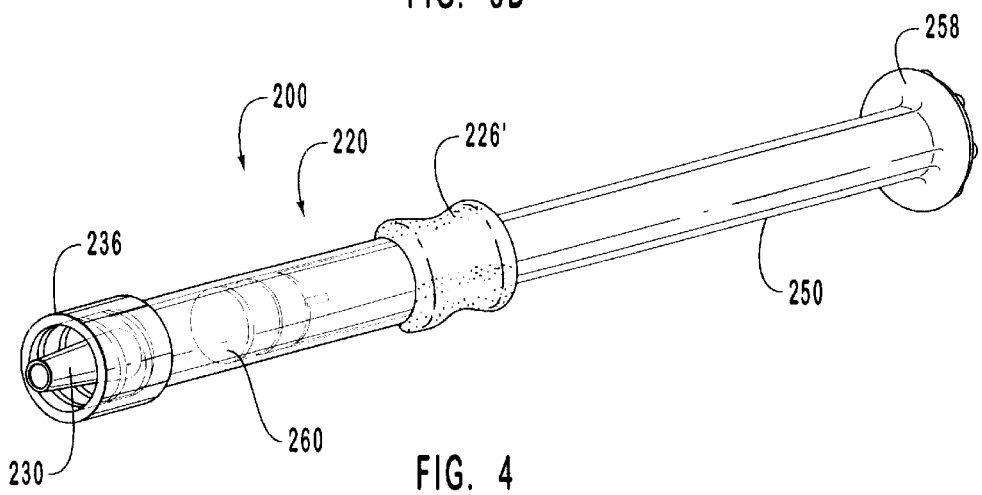
FIG. 4 is a side view of another embodiment of the inventive syringe.
Figure 5:
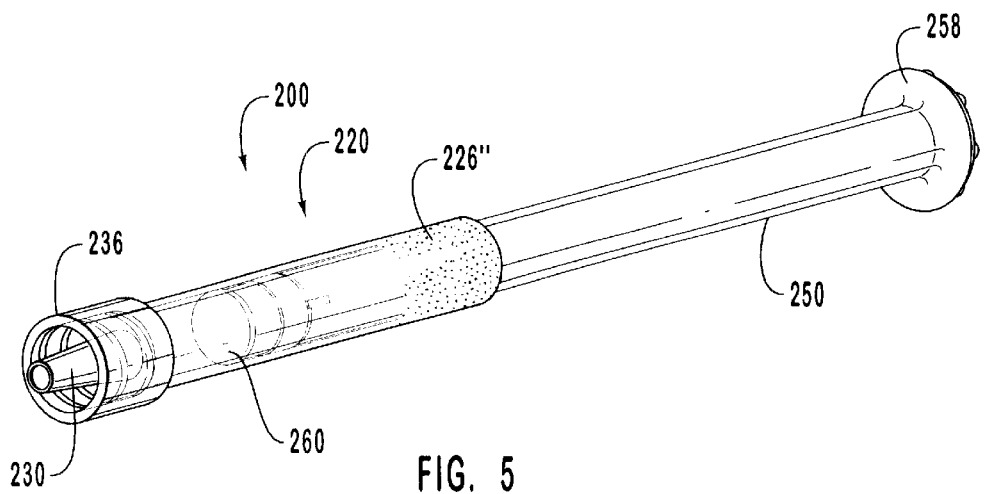
FIG. 5 is a side view of an additional embodiment of the inventive syringe.

Barrel 220 has a grasping handle 226 which is an annular flange extending radially and perpendicularly outward from sidewall 222 at top grasping end 221 of barrel 220. Grasping handle 226 is centrally located around opening 227 which has the same diameter as the interior surface 224 of chamber 225. Grasping handle 226 is an example of means for grasping the barrel such that a user's fingers can grasp the barrel. Additional examples of means for grasping the barrel include a raised engagement surface on the barrel as shown in FIG. 4 at 226', a textured engagement surface on the barrel as shown in a FIG. 5 at 226" or combinations of such surfaces. The engagement surface may be textured as shown by any suitable mechanism. Additionally, the engagement surface may be a smooth or textured groove around the perimeter of the barrel. As shown, the grasping handle 226 and the alternative grasping surfaces 226' and 226" are located at top grasping end 221 of barrel 220. While the grasping handle or grasping surface may also be located elsewhere on the barrel such as at bottom end 229, the location at top grasping end 221 is advantageous for several reasons. First, this enables a user to comfortably grasp the handle or surface of the barrel and the plunger. Additionally, it provides optimal visibility to the delivery site such that the user's view is not blocked by the user's fingers.

A radial extension 228 extends integrally from sidewall 222 at bottom end 229 inward to define an exit port 232. Exit port 232 is the opening which enables the composition in chamber 225 to exit. Radial extension 228 acts as a stop for plunger 250 as plunger 250 is depressed.

Exit port 232 is also the opening into channel 233 which enables channel 233 to communicate with chamber 225. Note that channel 233 is the interior surface of tapered exit tube 230. Channel 233 extends through tapered exit tube 230 and terminates at outlet 234.

Surrounding exit tube 230 is an attachment sleeve 236. Attachment sleeve 236 has an interior surface 237 with engagement threads 238 positioned thereon. A nozzle or tip 240, shown in FIGS. 3C and 3D, may be selectively attached to barrel 220 by coupling with threads 238. A variety of tips are available which may be attached such that channel 233 of exit tube 230 is in fluid communication with the tip for guided delivery of the composition to a desired location. Note that exit tube 230 and attachment sleeve 236 are integral parts of barrel 220.

Tip 240 is configured to selectively attach in fluid communication with exit tube 230. To accomplish this end, tip 240 has a threaded end 242 for engagement with threads 238 of attachment sleeve 236. Opposite threaded end 242 is a flexible and angled spout 244 for guiding delivery of the composition to a desired location. Different sizes and shapes of spouts can be used depending on the type and intended use of the composition. Furthermore, in alternative embodiments, tip 240 may be permanently attached to bottom end 229 or means for attaching the barrel to a tip 140 other than threads may be used to attach different sizes and/or shapes of tips. Additionally, syringes within the scope of the present invention need not necessarily utilize a separate tip or have an integral tip.

Plunger 250 has a distal lead end 251 opposite from a proximal pushing end 253 with a stem 252 extending therebetween. Plunger 250 is sized to be slidably received within chamber 225 through opening 227 at top grasping end 221. Plunger 250 has a length that permits it to be advanced to bottom end 229 while a significant portion of plunger 250 remains extending beyond opening 227. The length of plunger 250 is discussed in greater detail hereinbelow.

Radially extending outward at pushing end 253 of plunger 250 is an annular pushing handle 258 used in advancing plunger 250. Note that the pushing handle of the plunger is preferably configured as shown at 258 which is described in greater detail in U.S. Design Pat. No. 322,317. U.S. Design Pat. No. 322,317, which issued to Dan E. Fischer on Dec. 10, 1991 and is owned by Ultradent Products, Inc., is hereby incorporated by reference.

Figure 3A:
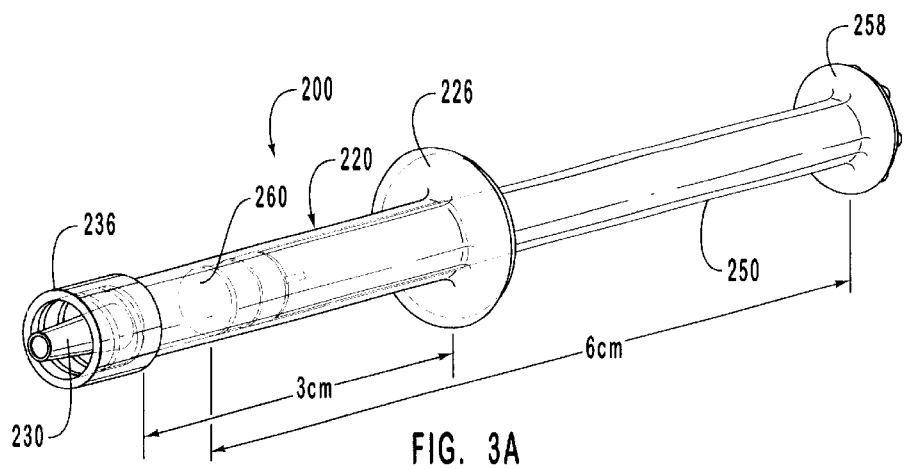
FIG. 3A is a perspective view of a syringe 200.
Figure 3B:
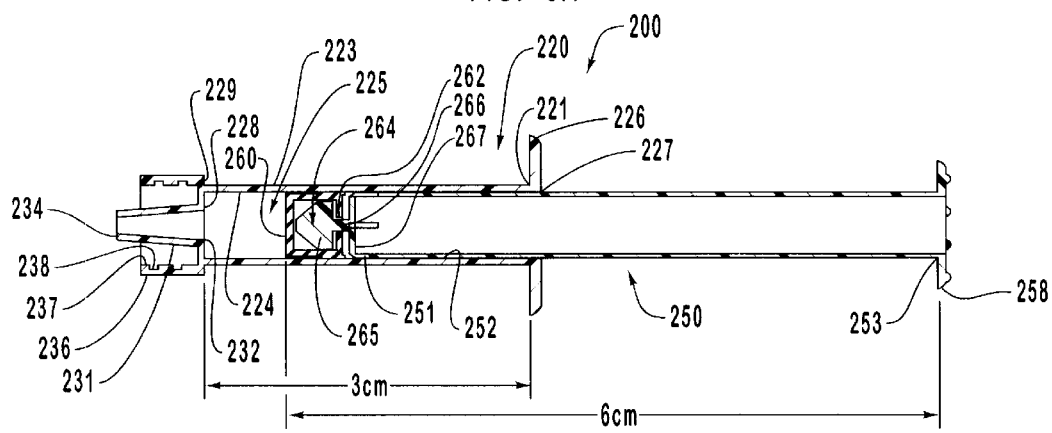
FIG. 3B is a cross-sectional view of the syringe 200 shown in FIG. 3A.

Positioned at lead end 251 of plunger 250 is a cylindrically shaped sealing gasket 260. More particularly, gasket 260 is coupled to stem 252 via a gasket holder as shown in FIG. 3B at 264. Gasket 260 is made of a soft, compressible, sealing material, such as rubber, which allows the exterior surface of gasket 260 to seal against interior surface 224 of chamber 225 as plunger 250 is advanced within chamber 225 or selectively slid down to bottom end 229. Gasket holder 264 has a post 266 with a head element 265 integrally extending at one end and a base 267 integrally extending from the other end. Head element 265 and post 266 are inserted into an opening 262 of gasket 260 which expands such that head element 265 can be inserted therein and then elastically return to its original size such that head element 265 is removably held in gasket 260. Base 267 is connected to stem 252 to hold gasket holder 264 in position.

A plunger within the scope of the present invention includes at least a stem and preferably also includes a handle such as pushing handle 258. The plunger may also include a gasket held by a gasket holder extending from a stem as discussed above. The plunger may also be shaped like the plunger shown and described in U.S. Pat. No. 4,986,820, which is hereby incorporated by reference. U.S. Pat. No. 4,986,820, which is entitled "Syringe Apparatus Having Improved Plunger", issued to Dan E. Fischer and is owned by Ultradent Products, Inc. Note that the entire plunger disclosed in U.S. Pat. No. 4,986,820 is integral. Another integral plunger is disclosed in U.S. patent application Ser. No. 09/504,738 which is hereby incorporated by reference. Ser. No. 09/504,738 which is also owned by Ultradent Products, Inc. is entitled "Syringe Apparatus Having a Plunger Tip with a Flexible Spring Lever and Related Methods and was filed on Feb. 16, 2000 for Kim L. Richardson and Richard N. Rachal. As described hereinbelow, specialized plungers may also be utilized which deploy a paddle. Examples of such specialized plungers are disclosed in U.S. patent application Ser. No. 09/356, 009 which is hereby incorporated by reference. Ser. No. 09/356,009 which is also owned by Ultradent Products, Inc. is entitled "Integrated Mixing and Dispensing Apparatus"

and was filed on Jul. 16, 1999 for Dan E. Fischer and Bruce McLean. In any event, as discussed below, plungers within the scope of the present invention are configured to be significantly longer than the length of the chamber of the barrel. The plungers disclosed herein are examples of plunger means for advancing the composition positioned within the barrel through the exit port at the first end of the barrel.

Figure 3C:
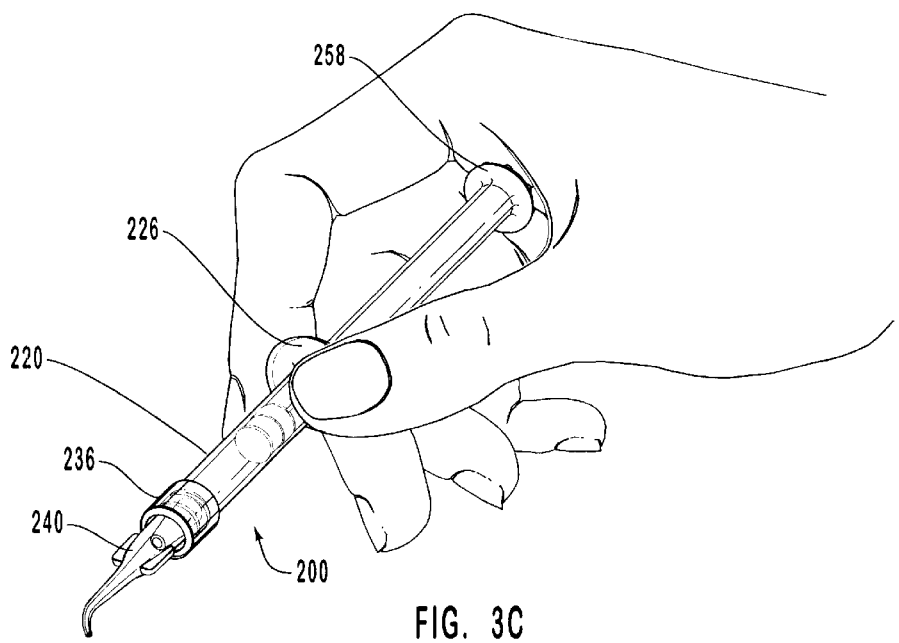
FIG. 3C is a perspective view of the syringe 200 shown in FIG. 3A loaded with a composition and with the plunger positioned to initially express the composition from the syringe.
Figure 3D:
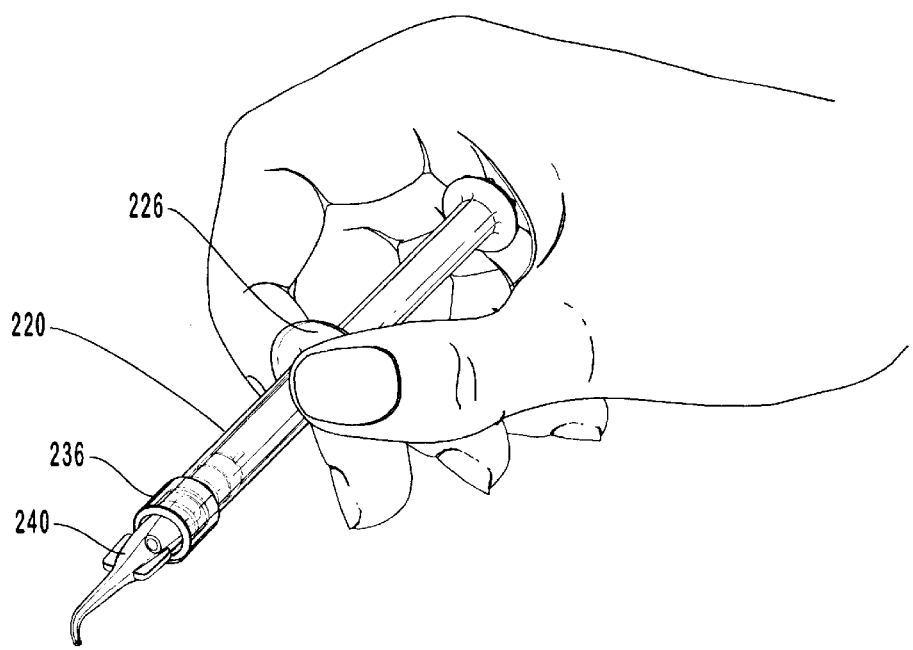
FIG. 3D is a perspective view of the syringe 200 shown in FIG. 3A after the plunger has been fully depressed to express all of the composition from the syringe.

Plunger 250 is shown having a length which is about twice as long as chamber 225. This is perhaps most clearly seen in FIG. 3D, wherein plunger 250 is fully advanced within chamber 225, since the portion of plunger 250 extending out of chamber 225 has a length that is at least equal to that of the portion of plunger 250 within chamber 225. This length provides a significant advantage over prior art syringes. For example, reference to syringe 100 as depicted in FIGS. 2C and 2D shows that a user must change hand positions as the plunger is depressed while reference to FIGS. 3C and 3D shows that the plunger can be fully depressed while holding syringe 200 in a single position.

To appreciate the importance of not altering the position in which the syringe is held, it is necessary to understand the manner in which such syringes are typically held and used. The grip shown being utilized in FIGS. 2C and 3C wherein the proximal pushing end of the plunger is pressed against the palm of the user's hand while the user's fingertips pull the grasping handle of the barrel to advance the plunger within the chamber is particularly useful in dentistry. This grip enables the user to deliver the composition contained in the chamber with a high degree of control. FIG. 2C shows the fingertips of the index finger and thumb positioned on grasping handle 126 while FIG. 3C shows a more secure grip. More particularly, FIG. 3C shows the fingertips of the middle finger, the index finger and the thumb holding grasping handle 226. Either grip may be utilized although, as mentioned, the grip shown in FIG. 3C is more secure and it also enables the user to apply greater pressure. In any event, these grips are useful in dentistry as they enable a user to hold the syringe in such a manner the user may maneuver the syringe as desired within a patient's mouth while maintaining a high degree of control.

As mentioned above, it is necessary to change the grip used with a conventional syringe such as that shown in FIGS. 2C and 2D. As plunger 150 is pushed farther into chamber 125, the user experiences increasing difficulty in pushing the plunger. More particularly, when the fingers are extended they can more easily push downward, however, as they draw closer to the palm with this particular grip the fingers do not have adequate strength to press grasping handle 126 toward the user's palm or toward pushing end 153 of barrel 120. The difficulty experienced makes it necessary for a user to shift from the position shown in FIG. 2C to that shown in FIG. 2D. This change in position may result in undesired movement of the syringe. As the grasp of the user is altered, the syringe may be inadvertently swung to the side away from the intended delivery site. The movement may be slight, however, some substances which may safely contact enamel or dentin can be potentially harmful to soft tissues such as the gums.

In addition to undesired movement of the syringe as well as the resulting interruption to a particular procedure, the configuration of syringe 100 increases the hand fatigue which a dental practitioner experiences. More particularly, many users attempt to compress a plunger into a chamber until it is necessary to regrasp the syringe due to the resistant experienced. Instead of stopping while it is still easy to compress, users typically strain to deliver the composition until the point is reached when it becomes to difficult for that particular hand grasp. When frequently repeated, this exertion can cause hand fatigue.

The length of plunger 250 relative to that of chamber 220 enables the syringe to be grasped in one position and then to be used to continuously deliver the composition in chamber 220 as shown in FIGS. 3C and 3D. As indicated above, this is a significant advantage as it eliminates the possibility of accidentally moving the syringe due to altering one's grasp of the syringe. Not only is it unnecessary to regrasp the syringe during the depression of plunger 250 into chamber 220, the configuration of syringe 200 also enables a user to exert less effort in delivering the composition. Further, the configuration enables a user to exert essentially the same amount effort throughout the depression of the plunger within the chamber of the barrel.

As indicated above, chamber 125 is designed to hold about 1.2 ml and the length of the chamber is about 5 cm while the length of the plunger is about 6 cm. The ratio of the length of plunger 150 to the length of the chamber 25 is accordingly, as also noted above, 1.2:1.

Plunger 250 is shown having a length which is about twice as long as chamber 225, as indicated above, so that the ratio of the length of the plunger to the length of the chamber is about 2:1. More particularly, when the chamber is designed to hold a composition ranging from about 0.2 ml to about 0.6 ml, then the length of the chamber is about 3 cm and length of the plunger is about 6 cm. The syringe shown at 200 depicts such a configuration. The length of the chamber is most preferably 3.15 cm when the barrel is used with a plunger having a length of about 6.2 cm; this yields a ratio of 1.97:1. While the preferred ratio is about 2:1, the ratio of the length of the plunger to the length of the chamber may also be no less than about 1.8:1 and still enable a user to deliver the entire content of the composition held in the chamber without regrasping the syringe. The ratio may even be as low as no less than about 1.5:1.

Chamber 225 can have any size and shape as long as the length of the chamber is significantly less than that of the length of the plunger, as discussed above. However, chamber 225 is preferably sized to hold small quantities of a composition. For example, as indicated above, chamber 225 of barrel 220 is preferably configured to hold an amount of a composition ranging from about 0.2 ml to about 0.6 ml. Chamber 225 is more preferably configured to hold an amount of a composition ranging from about 0.25 ml to about 0.3 ml. By utilizing a barrel having a chamber sized to hold such preferred volumes, the chamber and the plunger may have the optimal length ratios discussed above, which enable a user to easily deliver metered amounts as needed.

The preferred barrel volume corresponds with the amount needed of most dental compositions for a single use when utilized in particular procedures. While many compositions can be held in a syringe and used at various times, many dental compositions which are formed by mixing two parts cannot be used after a certain period of time has expired as the compositions may set or harden. In such instances, it is particularly desirable that the chamber hold no more than is necessary for the single use as any more will be wasted. Accordingly, limiting chamber 225 to holding small quantities of a composition, enables syringe 200 to be used for a single application without leaving any excess composition to be wasted. Since loading a syringe for unidosing requires less composition, the result is a less expensive procedure. Such unidoses are also sized appropriately for laboratory uses in dental schools as the dental students typically need only very small quantities.

FIGS. 6A–6D depict a set of syringes 200a–f held in a rack 10'. Syringes 200a–f are all configured such that the ratio of the length of the plunger to the length of the chamber is about 2:1 as it is for syringe 200. Accordingly, rack 10' holds a set of syringes that are all configured such that each syringe delivers small quantities of a composition. Such a set of syringes is ideal for completing an entire dental procedure such as a restoring a tooth with a dental composite material by delivering a sequence of materials as outlined above. Since only small amounts are needed, the entire system can be disposed of after the procedure is completed.

The parts of rack 10 are identified with the same numeral as those of rack 10 is the parts are the same and a prime symbol is used to denote those that are similar yet slightly different. Rack 10' has less cradles 20 than does rack 10. Note also that the spacing elements 30' of rack 10' are larger than those of rack 10 to prevent any overlap of the grasping handles 226. Note however that this configuration requires the use of more plastic than the compact configuration of rack 10. Syringes such as syringe 200 may be used with a rack such as rack 10' as shown in FIGS. 6A–6D or with a rack such as rack 10. Similarly, conventional syringes such as syringe 100 may be used with a rack such as rack 10 as shown in FIGS. 1A–1D or with rack 10'.

Unlike rack 10, the spacing elements 30' of rack 10' are not all identical. Note that terminal spacing elements 31a and 31b at opposite ends of rack 10' are narrower than the spacing elements 30' in the interior of rack 10'. It is not necessary for terminal spacing elements 31a and 31b to be wider since they are not sandwiched between two cradles 20.

Figure 6A:
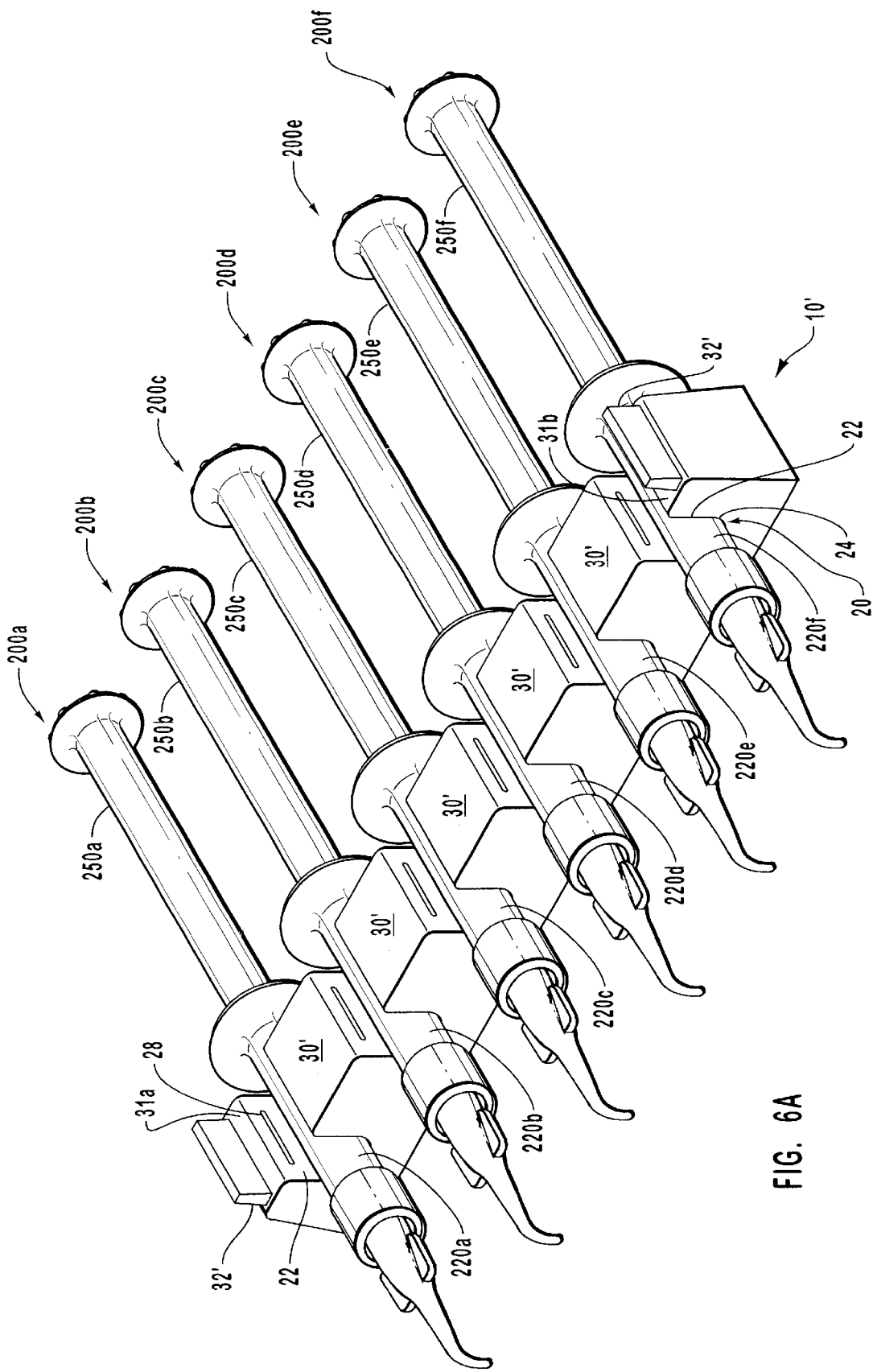
FIG. 6A is a perspective view of a rack 10' holding a set of syringes 200a–f.
Figure 6B:
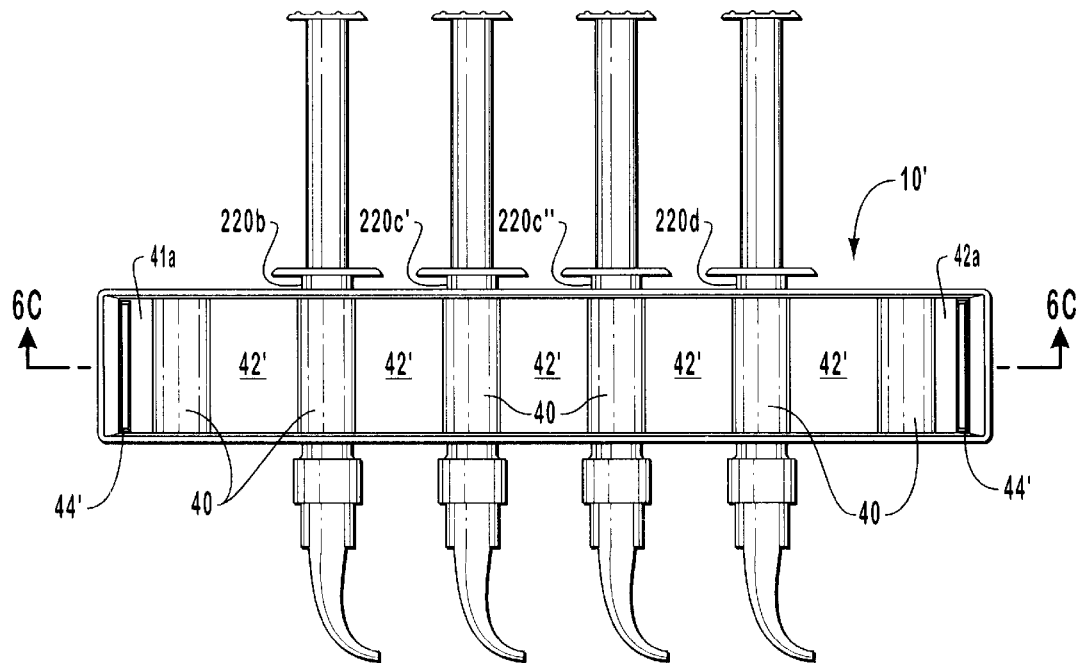
FIG. 6B is a bottom view of rack 10'.

FIG. 6B depicts the bottom view of rack 10' to show the hollow interior. Like rack 10, the rack 10' can be hollow as shown or solid. When rack 10 is hollow, as shown, the bottom side of each cradle 20 appears as a rounded swell 40 and the bottom side of each spacing element 30 appears as a flat surface 42'. Note that flat surfaces 41a and 41b are respective back sides of terminal spacing elements 31a and 31b.

In FIGS. 6A–6B it can be clearly seen that the length of each cradle 20 of rack 10' is just slightly less than the length of each barrel 220. Since barrel 220 is shorter than barrel 120, the ratio of the length of cradle 20 with respect to the ratio of barrel 220 is much closer than it is for barrel 120. More particularly, each cradle 20 has a length that is at least about ⅔ of the length of barrel 220. Since each barrel 220 is only slightly longer than each cradle 20, barrel 220 is more tightly held than barrel 120 of syringe 100.

Figure 6C:
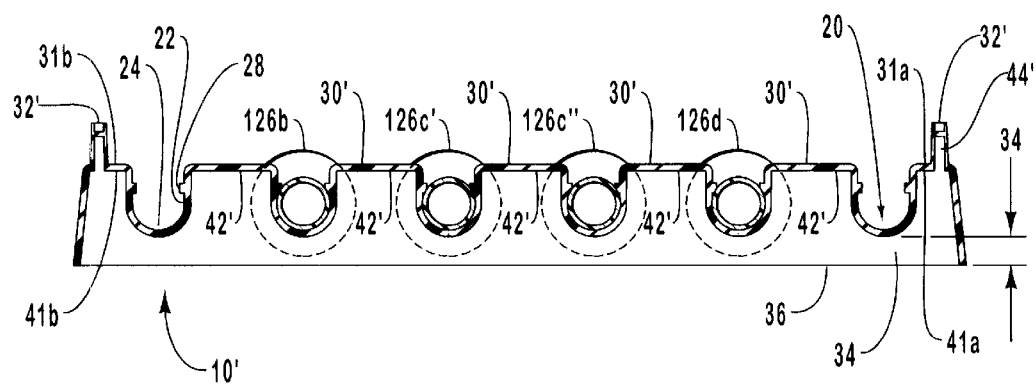
FIG. 6C is a longitudinal cross-sectional view of rack 10'.

FIG. 6C shows that platform portion 34 has a thickness between each bottom surface 24 of each cradle 20 and base surface 36 that is about the same as or greater than the length that each grasping handle 226 extends from each syringe barrel 120. As indicated with respect to rack 10, this configuration prevents the syringes 200 from being pivoted out of the cradles when rack 10' is placed on a flat surface. As also indicated with respect to rack 10, this configuration is beneficial for stacked racks as shown in FIG. 6D as it prevents the grasping handles 126 of the syringes in one set from becoming encumbered by the grasping handles 126 of the syringes in the adjacent set.

Figure 6D:
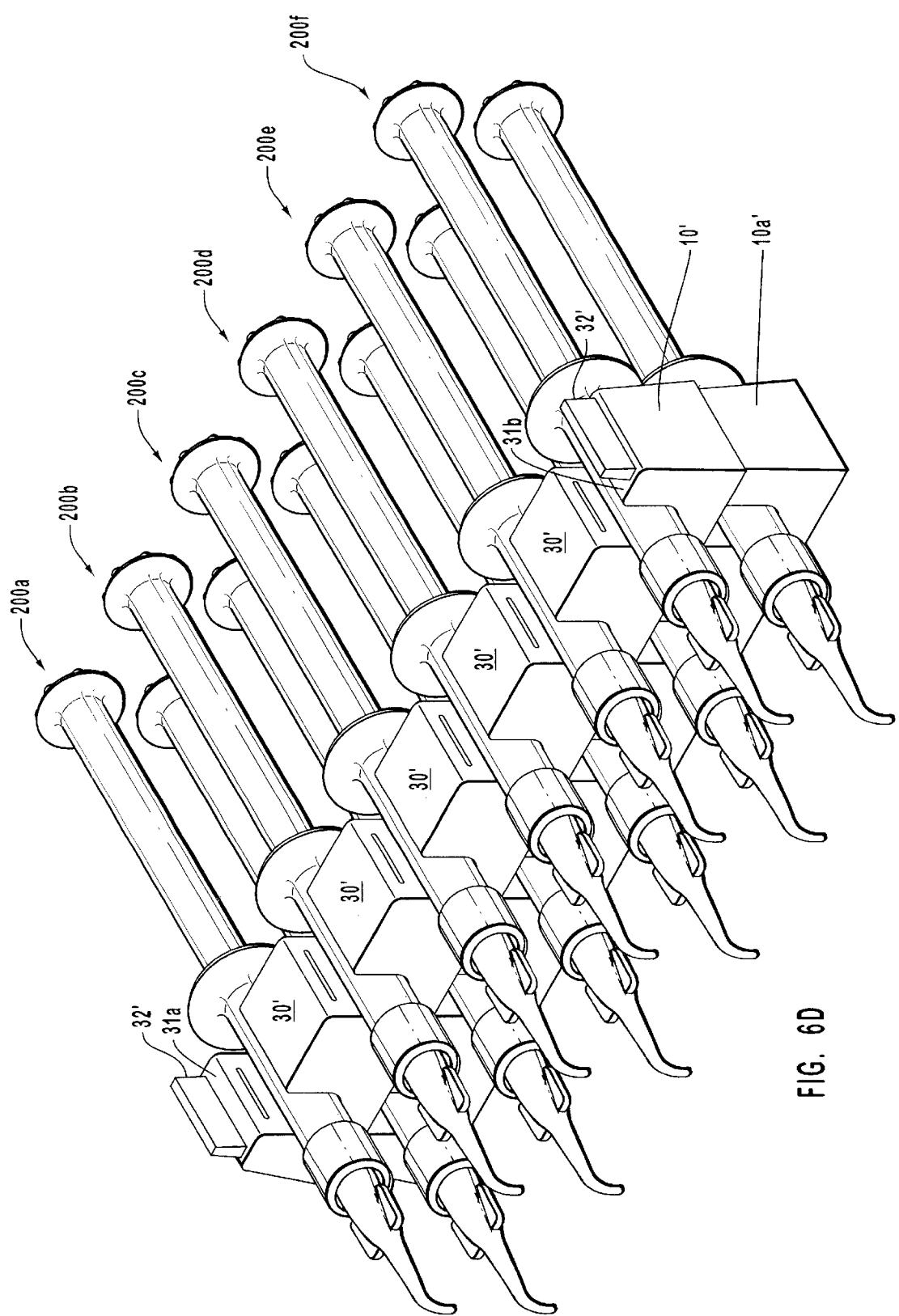
FIG. 6D is a perspective view of a rack 10' stacked on rack 10a'.

As with rack 10, rack 10' and rack 10a' have optional stacking prongs 32' as best seen in FIG. 6C and 6D. The optional stacking prongs 32' are shown extending from the terminal spacing elements 31a and 31b. However, the stacking prongs may extend from any of the spacing elements. Note that the stacking prongs 32' are rectangular while the stacking prongs 32 are conical. These stacking prongs are examples of means for stacking another rack on the rack in a manner that is secure yet detachable.

As indicated above, FIG. 6D depicts rack 10' positioned on rack 10a'. More racks can of course be stacked on rack 10' as needed. FIGS. 6A and FIG. 6D depicts rack 10' holding six syringes 200a–f. Syringes 200a–f may hold compositions like those described in reference to syringes 100a–f. FIGS. 6B–6C depict four syringes identified in the drawings as 200a, 200c', 200c" and 200d which may respectively hold an etchant, a bonding primer, a bonding resin and a flowable composite. The configuration of syringes 200c' and 200c" is not different from that of syringe 200c, however, the prime symbols are used to indicate that while 200c may hold a bonding agent syringes 200c' and 200c" may respectively hold a bonding primer and a bonding resin.

It will be appreciated that the present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by United States Letters Patent is:

1. A system for performing a procedure with syringes, the system comprising:
 a set of syringes, wherein each syringe in the set comprises:
  a hollow elongated syringe barrel defining a chamber containing a composition therein, and
  plunger means for advancing the composition contained within the chamber,
  wherein the length of the plunger means relative to the length of the chamber yields a ratio which is no less than about 1.5:1; and
 a rack adapted for holding the set of syringes,
  the rack having a base surface adapted to rest on a flat surface,
  the rack having a plurality of spacing elements configured such that a pair of spacing elements defines a cradle and such that the rack has a plurality of cradles,
  each cradle having opposing sides that integrally extend to a bottom to yield a slot configuration for easy removal and placement of the syringe barrel and to enable a user to simultaneously view the entire length of each syringe barrel held in the cradle while the syringe barrel rests on the bottom of the cradle,
  each cradle being configured such that the syringe barrels held in the cradles are in a plane that is parallel to that of the base surface of the rack and to a flat surface on which the base surface is resting.

2. A system as defined in claim 1, wherein the rack has a platform portion from which the spacing elements integrally extend and wherein the height of the platform portion between the bottom of each cradle and the base surface is sufficient to enable the cradles to hold the syringes above a flat surface on which the rack is resting so that the syringes are horizontal relative to the flat surface.

3. A system as defined in claim 1, wherein the syringe barrel of each syringe has a grasping handle extending radially outward from the barrel and wherein the length that the grasping handle extends from the syringe barrel is less than the height of the rack between the bottom of each cradle and the base surface.

4. A system as defined in claim 1, wherein the syringe barrel of each syringe has a grasping handle extending radially outward from the syringe barrel and wherein the length that the grasping handle extends from the syringe barrel is no greater than the width of each spacing element that is located between two cradles so that access to each cradle is not obstructed by a syringe in an adjacent cradle.

5. A system as defined in claim 1, wherein each syringe barrel of each syringe is round and wherein the bottom of each cradle is rounded to receive the round syringe barrels.

6. A system as defined in claim 1, wherein a locking extension extends slightly from each side of each cradle such that there is a tight fit with the syringe barrel of each syringe held in each cradle.

7. A system as defined in claim 1, wherein each cradle has a length that is less than about half of the length of the syringe barrel of the syringe held in each cradle.

8. A system as defined in claim 1, wherein each cradle has a length that is at least about ⅔ of the length of the syringe barrel of the syringe held in each cradle.

9. A system as defined in claim 1, wherein the rack has means for stacking another rack on the rack in a manner that is secure yet detachable.

10. A system as defined in claim 1, wherein the rack is hollow.

11. A system as defined in claim 1, wherein each syringe includes indicia to identify the composition contained within the syringe barrel.

12. A system for performing a procedure with syringes, the system comprising:
   a set of syringes, wherein each syringe in the set comprises a hollow elongated syringe barrel containing a composition and plunger means for advancing the composition contained within the syringe barrel; and
   a rack adapted for holding the set of syringes,
      the rack having a base surface adapted to rest on a flat surface,
      the rack having a plurality of spacing elements configured such that a pair of spacing elements defines a cradle and such that the rack has a plurality of cradles,
      each cradle having opposing sides that integrally extend to a bottom to yield a slot configuration for easy removal and placement of the syringe barrel and to enable a user to simultaneously view the entire length of each syringe barrel held in the cradle while the syringe barrel rests on the bottom of the cradle,
      each cradle being configured such that the syringes held in the cradles are in a plane that is parallel to that of the base surface of the rack and to a flat surface on which the base surface is resting, and
      the rack having prongs and recess that facilitate selective stacking and detachment of one rack from another rack.

13. A system as defined in claim 12, wherein the syringe barrel of each syringe has a grasping handle extending radially outward from the syringe barrel and wherein the length that the grasping handle extends from the syringe barrel is less than the height of the rack between the bottom of each cradle and the base surface.

14. A system as defined in claim 12, wherein the syringe barrel of each syringe has a grasping handle extending radially outward from the syringe barrel and wherein the length that the grasping handle extends from the syringe barrel is no greater than the width of each spacing element that is located between two cradles so that access to each cradle is not obstructed by a syringe in an adjacent cradle.

15. A system as defined in claim 12, wherein each syringe barrel of each syringe is round and wherein the bottom of each cradle is rounded to receive the round syringe barrels.

16. A system as defined in claim 12, wherein a locking extension extends slightly from each side of each cradle such that there is a tight fit with the syringe barrel of each syringe held in each cradle.

17. A system as defined in claim 12, wherein each cradle has a length that is less than about half of the length of the syringe barrel of the syringe held in each cradle.

18. A system as defined in claim 12, wherein each cradle has a length that is at least about ⅔ of the length of the syringe barrel of the syringe held in each cradle.

19. A system for performing a procedure with syringes, the system comprising:
   a set of syringes, wherein each syringe in the set has a hollow, round elongated syringe barrel containing a composition and plunger means for advancing the composition contained within the syringe barrel; and
   a rack adapted for holding the set of syringes,
      the rack having a base surface adapted to rest on a flat surface,
      the rack having a plurality of spacing elements configured such that a pair of spacing elements defines a cradle and such that the rack has a plurality of cradles,
      each cradle having opposing sides that integrally extend to a rounded bottom to yield a slot configuration for easy removal and placement of the syringe barrel and to enable a user to simultaneously view the entire length of each syringe barrel held in the cradle while the round elongated syringe barrel rests on the rounded bottom of the cradle,
      each cradle being configured such that the syringes held in the cradles are in a plane that is parallel to that of the base surface of the rack and to a flat surface on which the base surface is resting,
      each cradle having a locking extension extending slightly from each of its sides such that there is a tight fit with the syringe barrel of each syringe held in each cradle,
      wherein the rack has means for stacking another rack on the rack in a manner that is secure yet detachable.

20. A system as defined in claim 19, wherein the syringe barrel of each syringe has a grasping handle extending radially outward from the syringe barrel and wherein the length that the grasping handle extends from the syringe barrel is less than the height of the rack between the bottom of each cradle and the base surface.

21. A system as defined in claim 19, wherein the syringe barrel of each syringe has a grasping handle extending radially outward from the syringe barrel and wherein the length that the grasping handle extends from the syringe barrel is no greater than the width of each spacing element that is located between two cradles so that access to each cradle is not obstructed by a syringe in an adjacent cradle.

22. A system as defined in claim 19, wherein each cradle has a length that is less than about half of the length of the syringe barrel of the syringe held in each cradle.

23. A system as defined in claim 19, wherein each cradle has a length that is at least about ⅔ of the length of the syringe barrel of the syringe held in each cradle.

24. A system for performing a procedure with syringes, the system comprising:
   a set of syringes, wherein each syringe in the set comprises:
      a hollow, round elongated syringe barrel defining a chamber containing a composition therein, and a plunger for advancing the composition contained within the syringe barrel, the syringe barrel of each syringe having a grasping handle extending radially outward from the syringe barrel, wherein the length of the plunger relative to the length of the chamber yields a ratio which is no less than about 1.5:1; and a rack adapted for holding the set of syringes, the rack having a base surface adapted to rest on a flat surface, the rack having a plurality of spacing elements configured such that a pair of spacing elements defines a cradle and such that the rack has a plurality of cradles, each cradle having opposing sides that integrally extend to a bottom to yield a slot configuration for easy removal and placement of the syringe barrel and to enable a user to simultaneously view the entire length of each syringe barrel held in the cradle while the syringe barrel rests on the bottom of the cradle, each cradle being configured such that the syringes held in the cradles are in a plane that is parallel to that of the base surface of the rack and to a flat surface on which the base surface is resting, and each cradle having its bottom offset from the base surface such that the height between the bottom of each cradle and the base surface is greater than the length that the grasping handle of the syringe barrel extends from the syringe barrel to enable the cradles to hold the syringes horizontally above a flat surface on which the rack is resting.

25. A system as defined in claim 24, wherein the length that the grasping handle extends from the syringe barrel is no greater than the width of each spacing element that is located between two cradles so that access to each cradle is not obstructed by a syringe in an adjacent cradle.

26. A system as defined in claim 24, wherein each syringe barrel of each syringe is round and wherein the bottom of each cradle is rounded to receive the round syringe barrels.

27. A system as defined in claim 24, wherein a locking extension extends slightly from each side of each cradle such that there is a tight fit with the syringe barrel of each syringe held in each cradle.

28. A system as defined in claim 24, wherein each cradle has a length that is at least about ⅔ of the length of the syringe barrel of the syringe held in each cradle.

29. A system as defined in claim 24, wherein the rack has means for stacking another rack on the rack in a manner that is secure yet detachable.

30. A disposable system for performing a procedure with syringes, the system comprising:

a set of syringes, wherein each syringe includes:

a hollow elongated barrel with a sidewall extending between a top grasping end and an opposing bottom end, the sidewall having an interior surface defining a chamber for holding a composition, the barrel having an opening at the top grasping end for accessing the chamber and having an exit port at the bottom end for enabling the composition to exit the chamber, the barrel having means for grasping the barrel, the grasping means being located at the proximal grasping end of the barrel, and plunger means for advancing a composition held within the barrel, the plunger means including a distal lead end opposite from a proximal pushing end, the plunger means having a length which is sufficiently greater than that of the chamber to enable a user to grasp the syringe in a single position with the proximal pushing end against the palm of the user's hand and the user's fingertips against the grasping means and to then continuously deliver a composition from the chamber by advancing the plunger means within the chamber until the distal lead end of the plunger means contacts the bottom end of the chamber through pulling the grasping means while pushing the proximal pushing end against the user's palm; and a rack adapted for holding the set of syringes.

31. A system as recited in claim 30, wherein the rack has a base surface adapted to rest on a flat surface, wherein the rack has a plurality of spacing elements configured such that a pair of spacing elements defines a cradle and such that the rack has a plurality of cradles, wherein each cradle has opposing sides that integrally extend to a bottom to yield a slot configuration for easy removal and placement of the syringe barrel and to enable a user to simultaneously view the entire length of each syringe barrel held in the cradle while the syringe barrel rests on the bottom of the cradle, and wherein each cradle is configured such that the syringe barrels held in the cradles are in a plane that is parallel to that of the base surface of the rack and to a flat surface on which the base surface is resting.

32. A syringe as recited in claim 30, wherein the means for grasping the barrel is a grasping handle.

33. A system as recited in claim 30, wherein the chamber is sized such that it can hold only sufficient composition for use in a single dental restorative procedure.

34. A system as recited in claim 30, wherein the chamber is sized such that it can hold only a volume ranging from about m about 0.2 ml to about 0.6 ml.

35. A system as recited in claim 30, wherein the chamber is sized such that it can hold only a volume ranging from about m about 0.25 ml to about 0.3 ml.

36. A system as recited in claim 30, wherein the length of the plunger means relative to the length of the chamber yields a ratio which is no less than about 1.5:1.

37. A system as recited in claim 30, wherein the length of the plunger means relative to the length of the chamber yields a ratio which is no less than about 1.8:1.

38. A system as recited in claim 30, wherein the length of the plunger means relative to the length of the chamber yields a ratio which is about 2:1.

39. A disposable system for performing a procedure with syringes, the system comprising:

a set of syringes, wherein each syringe includes:

a hollow elongated barrel with a sidewall extending between a top grasping end and an opposing bottom end, the sidewall having an interior surface defining a chamber for holding a composition, the barrel having an opening at the top grasping end for accessing the chamber and having an exit port at the bottom end for enabling the composition to exit the chamber, the barrel having a grasping handle extending perpendicularly and radially from the sidewall at the proximal grasping end of the barrel, and a plunger positioned within the chamber of the barrel to advance the composition positioned within the barrel through the exit port at the bottom end of the barrel, the plunger having a length that is at least twice that of the chamber of the barrel such that when the plunger is fully advanced within the chamber a portion of the plunger extends out of the chamber with a length that is at least equal to that of the chamber; and a rack adapted for holding the set of syringes.

40. A system as recited in claim 39, wherein the rack has a base surface adapted to rest on a flat surface, wherein the rack has a plurality of spacing elements configured such that a pair of spacing elements defines a cradle and such that the rack has a plurality of cradles, wherein each cradle has opposing sides that integrally extend to a bottom to yield a slot configuration for easy removal and placement of the syringe barrel and to enable a user to simultaneously view the entire length of each syringe barrel held in the cradle while the syringe barrel rests on the bottom of the cradle, and wherein each cradle is configured such that the syringe barrels held in the cradles are in a plane that is parallel to that of the base surface of the rack and to a flat surface on which the base surface is resting.

41. A system as recited in claim 39, wherein the chamber is sized such that it can hold only sufficient composition for use in a single dental restorative procedure.

42. A system as recited in claim 39, wherein the chamber is sized such that it can hold only a volume ranging from about m about 0.2 ml to about 0.6 ml.

43. A system as recited in claim 39, wherein the chamber is sized such that it can hold only a volume ranging from about m about 0.25 ml to about 0.3 ml.

44. A method for performing a procedure with disposable syringes sized for a single application, the method comprising:

obtaining a set of syringes held in a rack for sequential use, each syringe comprising a hollow elongated syringe barrel with a chamber sized to hold only sufficient composition for a single application, each syringe containing a different composition in its respective chamber, wherein the barrel has means for grasping the barrel located at the proximal grasping end of the barrel, wherein the plunger means has a distal lead end opposite from a proximal pushing end;

sequentially removing each syringe from the rack and delivering the composition held in the chamber of each syringe barrel by depressing a plunger means for advancing the composition positioned within the chamber out of the syringe barrel, wherein depressing the plunger means involves grasping the syringe with the proximal pushing end of the plunger means against the palm of the user's hand and with the user's fingertips against the grasping means; and continuously delivering the composition from the chamber by advancing the plunger means within the chamber until the distal lead end of the plunger means contacts a bottom end of the chamber through pulling the grasping means while pushing the proximal pushing end against the user's palm, without regrasping the syringe such that the syringe is not moved relative to a delivery site during the delivery of the composition to the delivery site due to movement of the user's hand; and discarding the set of syringes and the rack after delivering the composition held in the chamber of each syringe barrel to complete the procedure.

45. A method as recited in claim 44, wherein the procedure is a dental restorative procedure.

46. A method as recited in claim 44, wherein the rack has a base surface adapted to rest on a flat surface, wherein the rack has a plurality of spacing elements configured such that a pair of spacing elements defines a cradle and such that the rack has a plurality of cradles, wherein each cradle has opposing sides that integrally extend to a bottom to yield a slot configuration for easy removal and placement of the syringe barrel and to enable a user to simultaneously view the entire length of each syringe barrel held in the cradle while the syringe barrel rests on the bottom of the cradle, and wherein each cradle is configured such that the syringe barrels held in the cradles are in a plane that is parallel to that of the base surface of the rack and to a flat surface on which the base surface is resting.

47. A method as recited in claim 44, wherein the barrel has means for grasping the barrel located at the proximal grasping end of the barrel, wherein the plunger means has a distal lead end opposite from a proximal pushing end, and wherein depressing the plunger means involves grasping the syringe with the proximal pushing end of the plunger means against the palm of the user's hand and with the user's fingertips against the grasping means, and continuously delivering the composition from the chamber by advancing the plunger means within the chamber until the distal lead end of the plunger means contacts a bottom end of the chamber through pulling the grasping means while pushing the proximal pushing end against the user's palm, without regrasping the syringe such that the syringe is not moved relative to a delivery site during the delivery of the composition to the delivery site due to movement of the user's hand.

48. A method as recited in claim 44, wherein the chamber is sized such that it can hold only a volume ranging from about 0.2 ml to about 0.6 ml.

49. A method as recited in claim 44, wherein the chamber is sized such that it can hold only a volume ranging from about m about 0.25 ml to about 0.3 ml.

50. A method as recited in claim 44, wherein the length of the plunger means relative to the length of the chamber yields a ratio which is no less than about 1.5:1.

51. A method as recited in claim 44, wherein the length of the plunger means relative to the length of the chamber yields a ratio which is no less than about 1.8:1.

52. A method as recited in claim 44, wherein the length of the plunger means relative to the length of the chamber yields a ratio which is about 2:1.

53. A method as recited in claim 44, wherein the plunger means has a length that is at least twice that of the chamber of the barrel such that when the plunger means is fully advanced within the chamber a portion of the plunger extends out of the chamber with a length that is at least equal to that of the chamber.

* * * * *

UNITED STATES PATENT AND TRADEMARK OFFICE
CERTIFICATE OF CORRECTION

PATENT NO.    : 6,540,072 B1
DATED         : April 1, 2003
INVENTOR(S)   : Dan E. Fischer Page 1 of 1

It is certified that error appears in the above-identified patent and that said Letters Patent is hereby corrected as shown below:

Column 1,
Line 19, before "a system" please insert -- to --

Column 2,
Line 40, after "held in" please insert -- a --

Column 3,
Line 46, after "amount" please insert -- of --

Column 4,
Line 61, after "cradles in" please insert -- a --

Column 6,
Line 47, before "bonding primer" please change "PERMAQUI-CK®" to
-- PERMAQUICK® --

Column 10,
Line 60, before "and was filed" please delete "Methods" and insert -- Methods" --

Column 11,
Line 65, after "due to the" please delete "resistant" and insert -- resistance --

Column 12,
Line 15, after "amount" please insert -- of --

Signed and Sealed this

Ninth Day of December, 2003

JAMES E. ROGAN
*Director of the United States Patent and Trademark Office*